United States Patent
Bontus et al.

(10) Patent No.: US 7,430,270 B2
(45) Date of Patent: Sep. 30, 2008

(54) COMPUTERIZED TOMOGRAPHY METHOD WITH HELICAL RELATIVE MOVEMENT AND CONICAL BEAM

(75) Inventors: Claas Bontus, Aachen (DE); Thomas Kohler, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/570,101

(22) PCT Filed: Jun. 9, 2005

(86) PCT No.: PCT/IB2005/051904
§ 371 (c)(1), (2), (4) Date: Dec. 6, 2006

(87) PCT Pub. No.: WO2005/121836
PCT Pub. Date: Dec. 22, 2005

(65) Prior Publication Data
US 2008/0013676 A1  Jan. 17, 2008

(30) Foreign Application Priority Data
Jun. 9, 2004  (DE) .............................. 041 02 608

(51) Int. Cl.
*H05G 1/60* (2006.01)
(52) U.S. Cl. ............................................. 378/17; 378/4
(58) Field of Classification Search ............... 378/4–20, 378/901
See application file for complete search history.

(56) References Cited
U.S. PATENT DOCUMENTS
4,769,757 A  9/1988  Horiba et al.
4,979,111 A  12/1990  Nishimura
6,529,575 B1 *  3/2003  Hsieh ............................. 378/4

(Continued)

FOREIGN PATENT DOCUMENTS
EP  0 429 191 A2  5/1991

(Continued)

OTHER PUBLICATIONS
Kohler et al., Evaluation of helical cone-beam CT reconstruction algorithms, Nov. 10-16, 2002, Nuclear Science Symposium Conference Record, 2002 IEEE, vol. 2, pp. 1217-1220.*

(Continued)

*Primary Examiner*—Courtney Thomas
*Assistant Examiner*—Alexander H Taningco

(57) ABSTRACT

The invention relates to a computerized tomography method, wherein a radiation source executes an nPi relative movement along a helix with respect to an object. Acquired measured values are partially derived according to the angular position of the radiation source on the helix and intermediate filter values are generated by filtering the derived measured values along the filter lines with a k filter. Each intermediate filter value is multiplied by a filter factor, where the filter factor for intermediate filter values that have been generated by filtering the derived measured values along filter lines, which run exclusively within the Pi window, is greater than or equal to those filter factors by which the intermediate filter values are multiplied, which have been generated by filtering the derived measured values along filter lines, which run inside as well as outside the Pi window. The intermediate filter values assigned to a measured value are added to a filter value and the filter values are back-projected for reconstruction of a CT image.

20 Claims, 10 Drawing Sheets

U.S. PATENT DOCUMENTS

Figure 1:
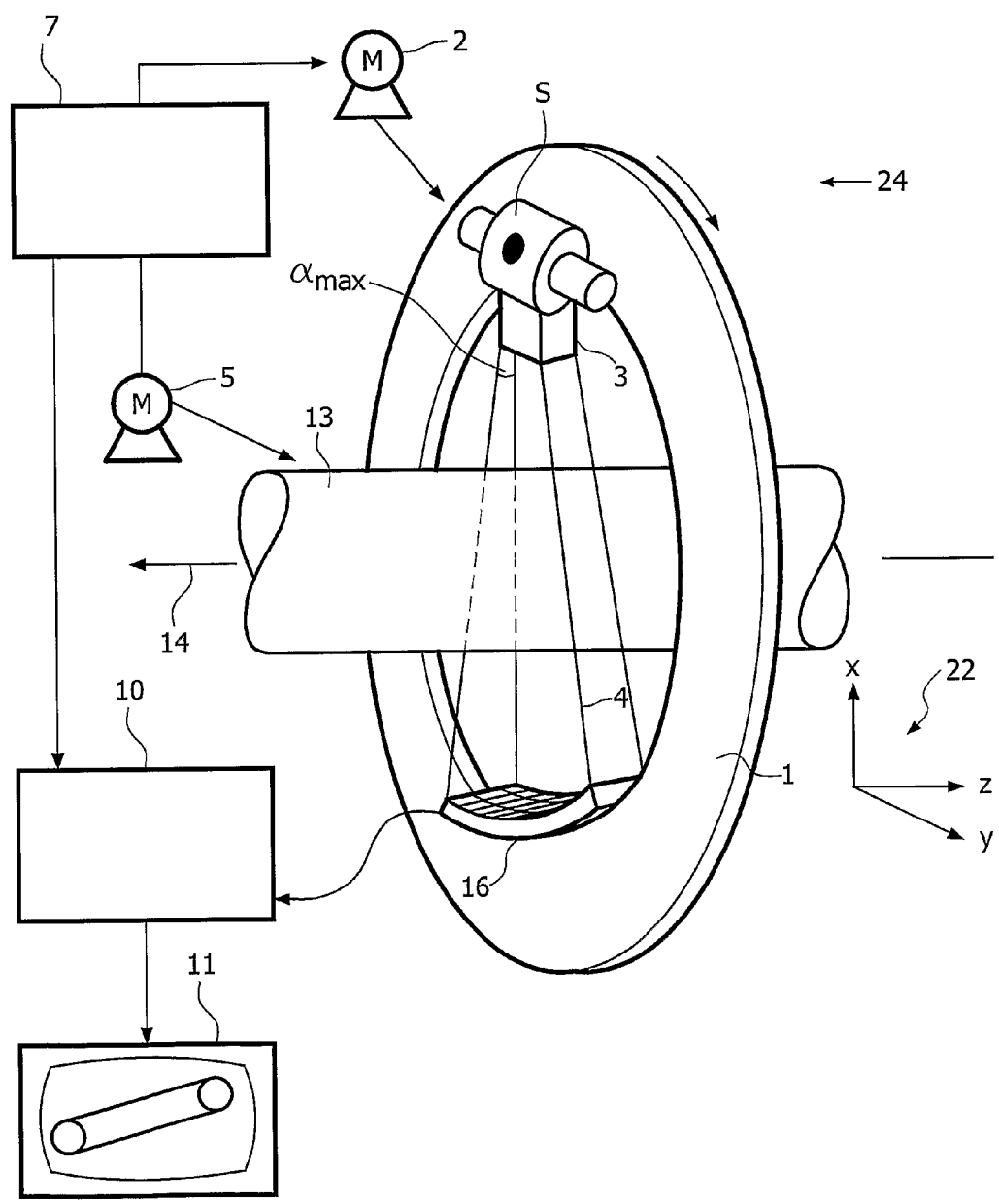

| | | | | |
|---|---|---|---|---|
| 6,542,572 B2* | 4/2003 | Danielsson et al. | ............ | 378/15 |
| 6,574,299 B1* | 6/2003 | Katsevich | .................... | 378/15 |
| 7,010,079 B2* | 3/2006 | Katsevich | ...................... | 378/4 |
| 2003/0161444 A1* | 8/2003 | Katsevich | .................. | 378/210 |
| 2004/0028173 A1* | 2/2004 | van der Haar | .................. | 378/4 |
| 2006/0233294 A1* | 10/2006 | Bontus et al. | .................. | 378/4 |

OTHER PUBLICATIONS

Proksa et al., The n-Pi-Method for Helical Cone-beam CT, IEEE Transactions on Medical Imaging, vol. 19, No. 9, Sep. 2000, pp. 848-863.*

Katsevich, Analysis of an exact inversion algorithm for spiral cone-beam CT, Physics in Medicine and Biology, 47, 2002, pp. 2583-2597.*

Katsevich, A.; Analysis of an exact inversion algorithm for spiral cone-beam CT; 2002, Phys. Med. Biol.; 47:2583-2597.

Proksa, R., et al.; The n-PI-Method for Helical Cone-Beam CT; 2000; IEEE Trans. on Medical Imaging; 19(9) 848-863.

* cited by examiner

COMPUTERIZED TOMOGRAPHY METHOD WITH HELICAL RELATIVE MOVEMENT AND CONICAL BEAM The invention relates to a computerized tomography method, in which an examination area is irradiated by a conical beam along a helical trajectory. The invention also relates to a computer tomograph as well as a computer program for controlling the computer tomograph.

In known methods of the type mentioned in the opening paragraph, the spatial path of the absorption or weakening of the radiation, as the case may be, in the examination area can be reconstructed from the measured values acquired by a detecting unit with a detector surface. Exact reconstruction methods can then be used, which yield a better quality of the reconstructed quality compared to the approximative methods.

The disadvantage of known exact reconstruction methods based on Radon inversion is that they entail very high computation expenditure. Another known reconstruction method (hereafter designated as κ-method), which is known from "Analysis of an Exact Inversion Algorithm for Spiral Cone-Beam CT", Physics Medicine and Biology, vol. 47, pp. 2583-2597, uses a filtered back-projection and requires lower computation expenditure than the methods based on a Radon inversion. The κ-method uses measured values, which are present on the detector surface in what is called a Pi window. The Pi window is the area of the detector surface, which detects the partial beam of the conical beam that is bounded by two windings of the helical trajectory, neighboring the respective radiation source position. This means that the Pi window is bounded by projections of the windings of the helical trajectory, which are arranged adjacent to the respective radiation source position. These projections are henceforth designated as Pi boundary lines. The Pi window and the Pi boundary lines are explained in some more detail below. Measured values lying outside the Pi window on the detector surface are not taken into consideration in the κ-reconstruction method. This results in a poor signal-to-noise ratio. Besides, the κ-method reduces the distance between the two neighboring windings of the helical trajectory. If the distance is too small, the detector surface is large in relation to the Pi window and more measured values are acquired than needed for reconstruction. This entails an unnecessarily high radiation burden in the examination of a patient. On the other hand, if the distance between two neighboring windings is too large, the partial beam bounded by neighboring windings is not completely detected by the detector surface i.e. the Pi window is larger than the detector surface, so not enough measured values are detected for an exact reconstruction. A variation of the distance between two neighboring windings of the helical trajectory is thus possible only with high restrictions, though it is often required, particularly in medical examinations.

It is therefore an object of the present invention to indicate a computerized tomography method that makes reconstruction of a CT image possible, whose quality corresponds at least to the quality of a CT image, which has been reconstructed by the κ-method, where similarly low computing expenditure is needed and where the distance between neighbouring windings of the helical trajectory is variable over a wide range. This object is achieved by the invention by means of a computerized tomography method comprising the following steps of:
a) Generation of a conical beam (4) traversing an examination area (13) by means of a radiation source (S),
b) Generation of a helical nPi relative movement between the radiation source (S) and the examination area (13),
c) Acquisition of the measured values, which depend on the intensity in the beam (4) by means of a detector unit, where a ray of the beam (4) is assigned to each measured value,
d) Reconstruction of a CT image by means of the steps of:
Derivation of the measured values partially according to the angular position of the radiation source,
Generation of intermediate filter values, where an intermediate filter value is generated by filtering a derived measured value, which lie in an nPi window, along an associated filter line with a κ-filter, and where, for at least one of those derived measured values, more than one filter line is associated, and
Multiplication of each intermediate filter value by a filter factor, where each intermediate filter value that has been generated by filtering the derived measured value along filter lines, which run exclusively within the Pi window, is multiplied by a filter factor, which is greater than or equal to the filter factors by which the other intermediate filter values are multiplied,
Adding the weighted intermediate filter values of each measured value that lies in the nPi window to each respective filter value,
Reconstruction of the CT image by back-projection of the filter values.

Generally, in such a tomography method a conical beam traversing the examination area is generated. The examination area is provided to put an object under investigation in it, i.e. a patient or a part of a patient. The radiation source and the examination area perform a helical movement relatively to each other. For example, such established kind of movement can be characterized by a rotation around an axis of rotation and a shift in a direction of shift parallel to the axis of rotation, so that is has the shape of a helix. The radiation source position on the helix can generally be defined by an angular position. The intensity in the beam can be detected by a detector unit located opposite to the radiation source.

The nPi relative movement or the nPi acquisition is also generally known. In this special relative movement, the pitch i.e. the distance of neighboring windows of the helical trajectory are selected such that n+1 windings are projected on the detector surface of a detector unit from each radiation source position, where n is a natural odd number greater than 1. As a rule, the 3Pi-, 5Pi-, 7Pi-etc. relative movement or acquisition is talked about. The projections of the windings of the helical trajectory on the detector surface are designated as in Pi boundary lines with m=1, 3, . . . , n. The two innermost projected windings are the Pi boundary lines, the two windings projected neighboring the Pi boundary lines are the 3Pi boundary lines, then the 5Pi-boundary lines will follow etc. The path of the mPi boundary lines on the detector surface will be elucidated in greater detail below.

The area of the detector surface lying between the Pi boundary lines is designated as Pi window. In general, the area of the detector surface lying between the mPi boundary lines is designated as mPi window.

A CT image is reconstructed from the measured values by derivate partially the measured values according to the angular position of the radiation source. That means for example, that the measured values which are assigned rays run in parallel and originate from different radiation source positions are derived partially according to the angular position of the radiation source of the ray which is assigned to the respective measured value.

In another step of the inventive method intermediate filter values are generated. That means, for example, a generation of intermediate filter values by filtering of the derived measured values, which lie in an nPi window, along filter lines with a κ-filter, where some of the filter lines run inside as well as outside a Pi window, where several filter lines are assigned to at least a part of the measured values and where an intermediate filter value is generated per measured value and its associated filter line, so that one or more intermediate filter values are assigned to each measured value, which lies in the nPi window.

In another step of the inventive method the intermediate filter values are weighted. This means, for example, a multiplication of each intermediate filter value by a filter factor, where each intermediate filter value that has been generated by filtering the derived measured value along filter lines, which run exclusively within the Pi window, is multiplied by a filter factor, which is greater than or equal to those filter factors by which the intermediate filter values are multiplied which have been generated by filtering the derived measured values along filter lines, which run inside as well as outside the Pi window. The weighted intermediate filter values are added. This means, for example, adding the weighted intermediate filter values of each measured value that lies in the nPi window to each respective filter value, so that a filter value is assigned to each measured value that lies in the nPi window. A CT image is generated by a reconstruction of the filter values.

As mentioned above, the known κ-method is restricted to a certain pitch. In contradiction, the method as invented is not restricted to such a pitch, so that the pitch is variable over a large area. It has also turned out that the generation, as invented, of intermediate filter values by filtering the measured values and that the multiplication of the intermediate filter values by filter factors generated through filter lines for intermediate filter elements that run exclusively within the Pi window, are greater than or equal to the other intermediate filter values, leads to qualitatively very good CT images. As these CT-images are reconstructed by means of back projection, the calculation cost is relatively small and similar to the calculation cost in case of the κ-method. It further turned out that the reconstruction subsequent to the nPi acquisition also uses filter values, which were generated by filtering of measured values, which are outside the Pi window. This provides a better signal-to-noise ratio in comparison with the κ-method, which uses measured values only within the PI window.

Claim 2 represents a preferred type of filtering, which helps achieve good quality CT images. The image quality is further raised by using the filter lines described in the claims 3, 6, 7 and 8. Another improvement in the image quality is achieved by using the filter directions and filter factors described in the claims 4 and 5.

Claim 9 describes a computer tomograph for carrying out the method as invented. Claim 10 defines a computer program for controlling a computer tomograph as claimed in claim 9.

Figure 2:
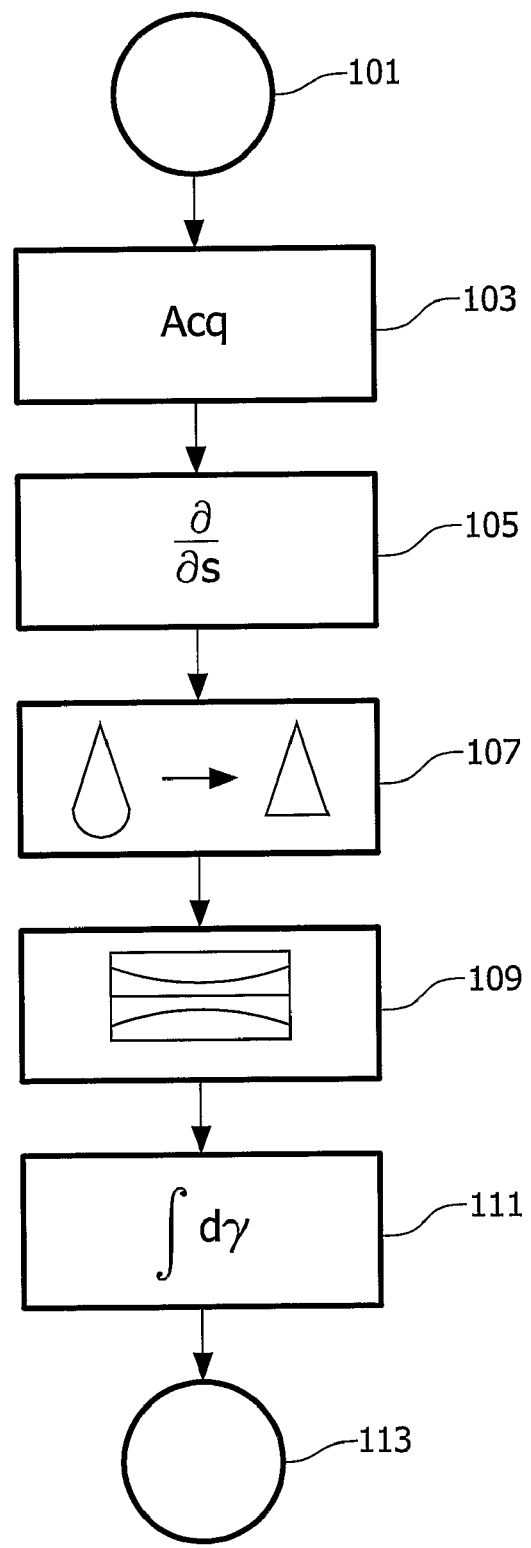
Figure 3:
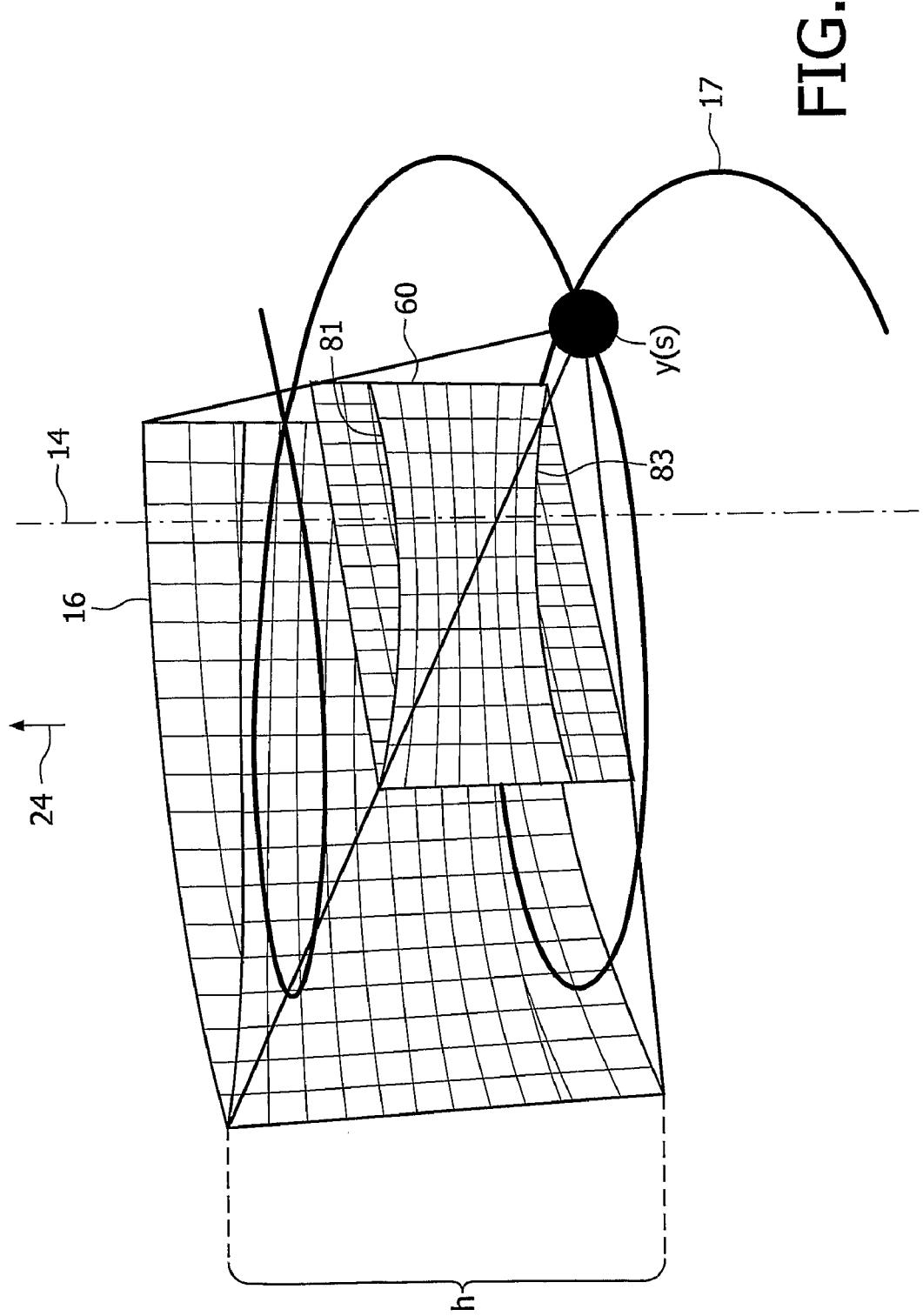
Figure 4:
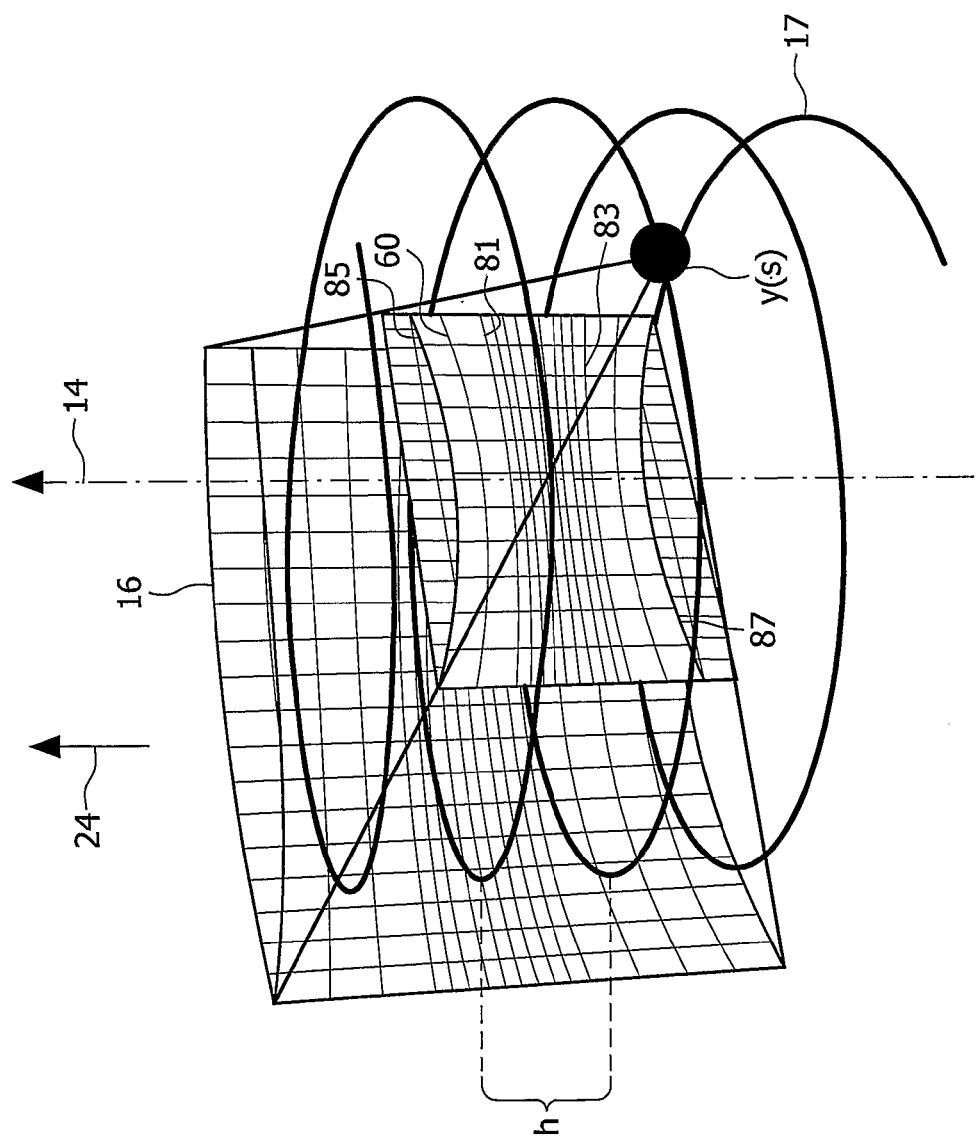
Figure 5:
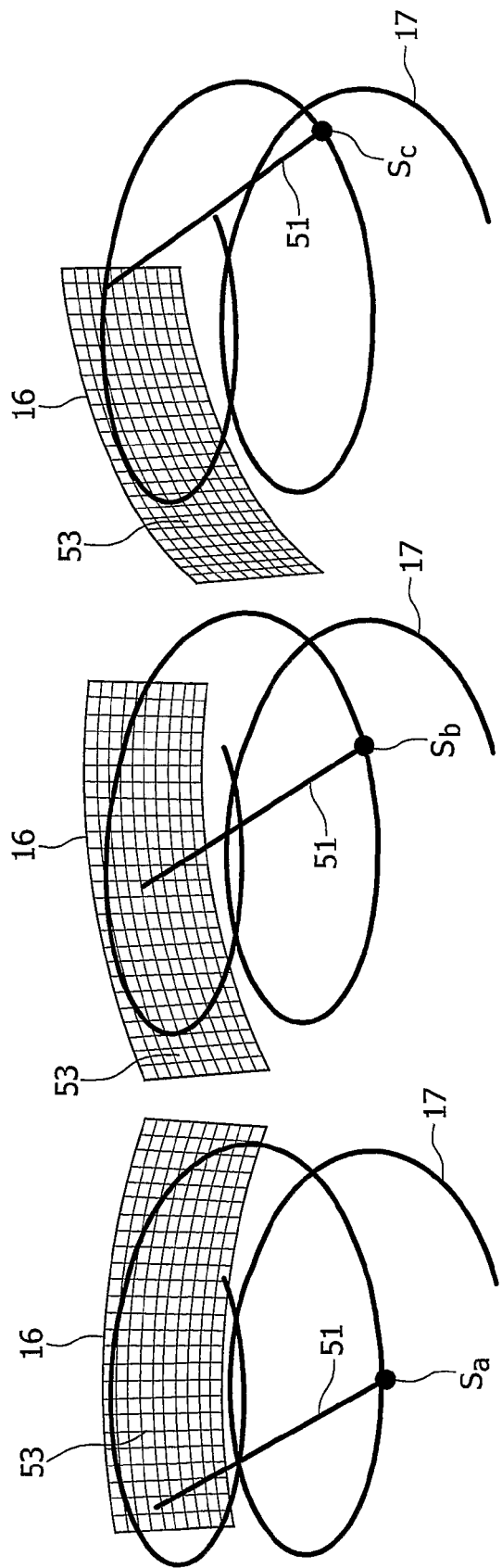
Figure 6:
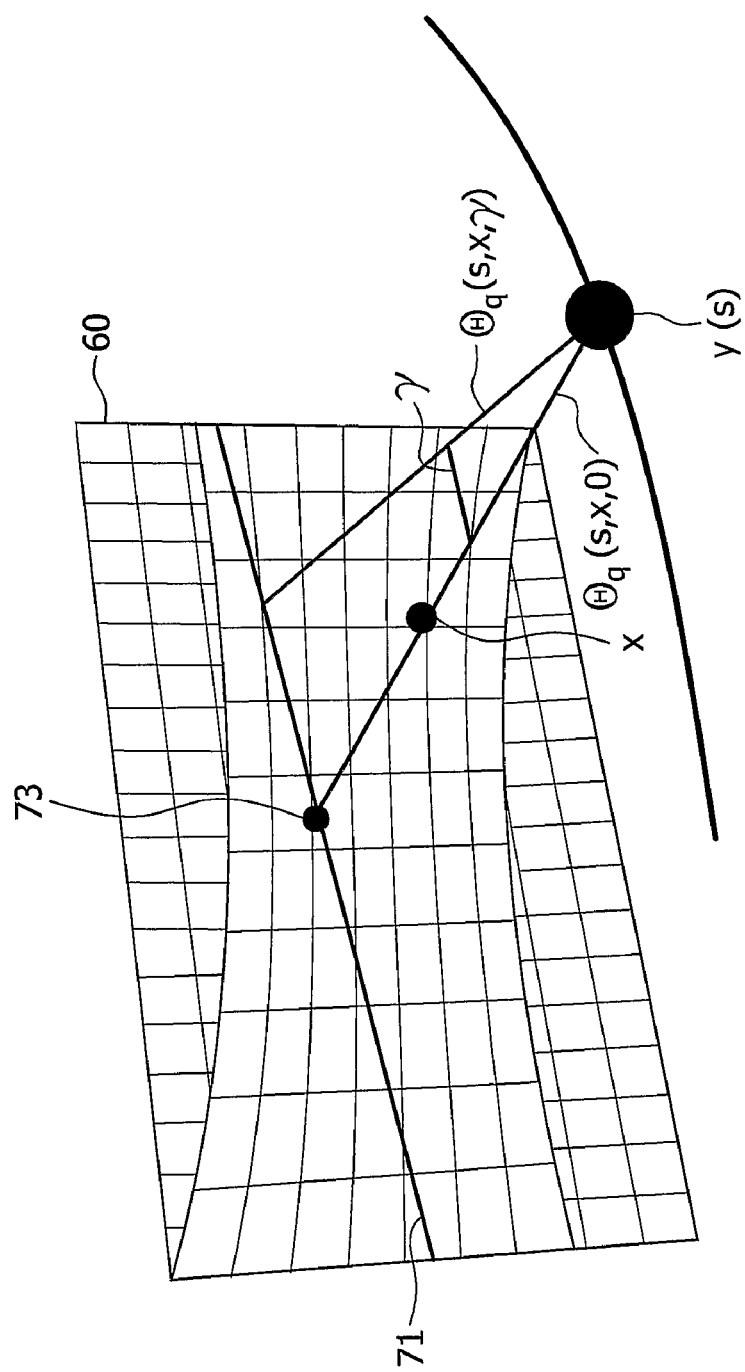
Figure 7:
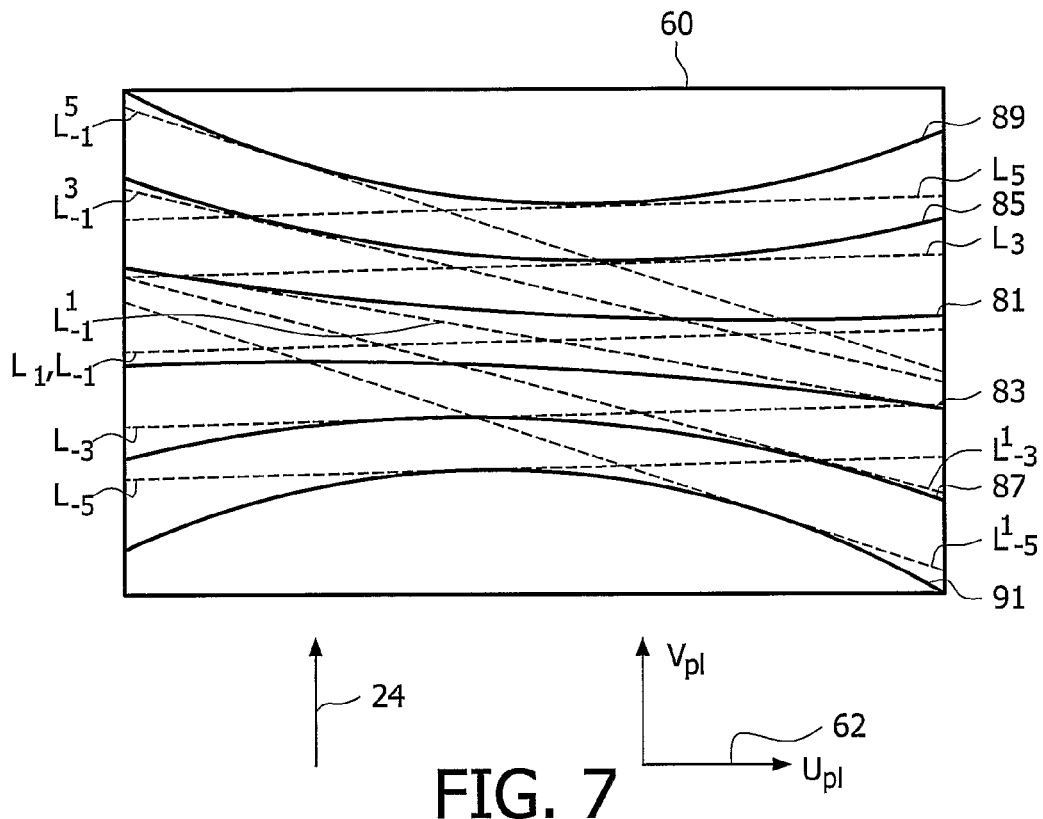
Figure 8:
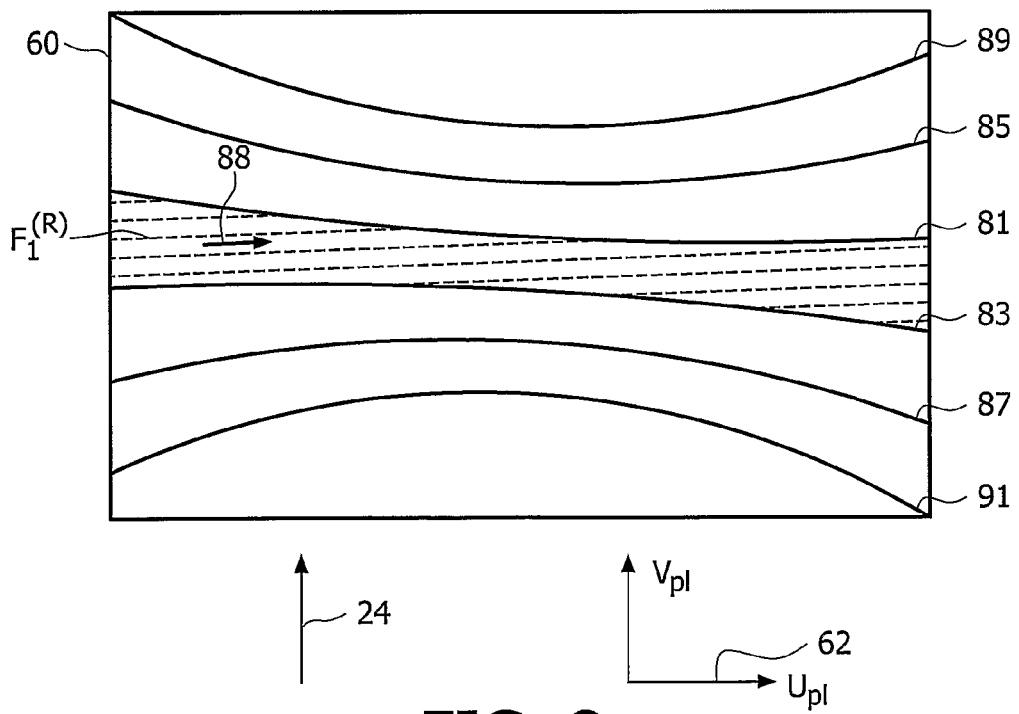
Figure 9:
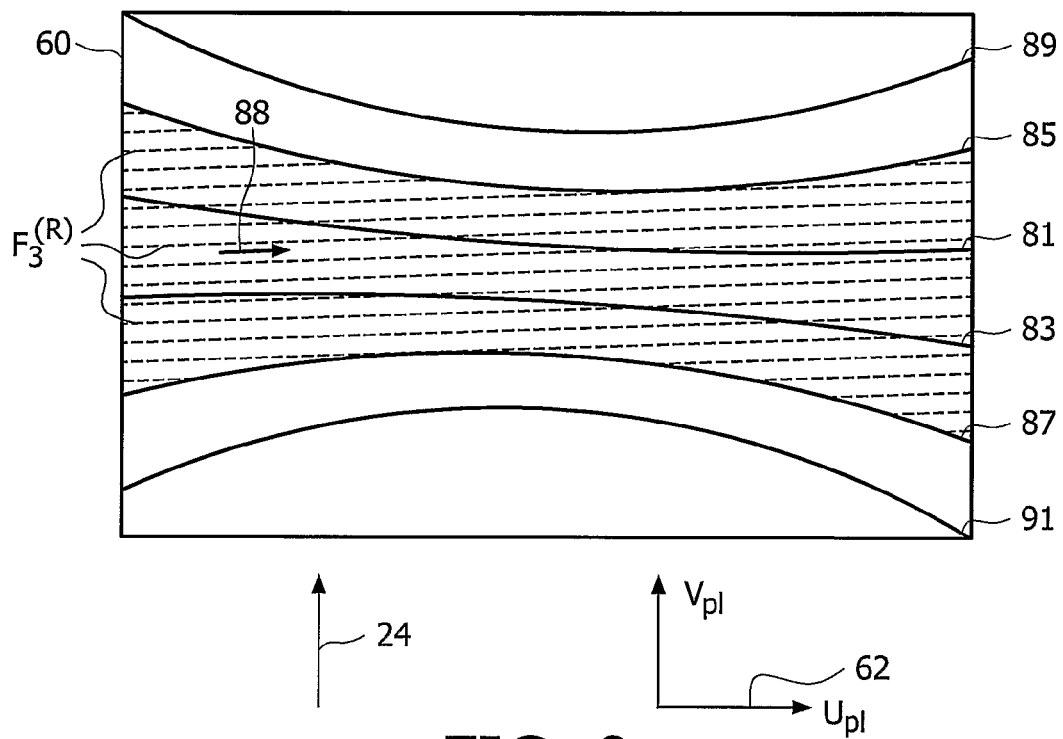
Figure 10:
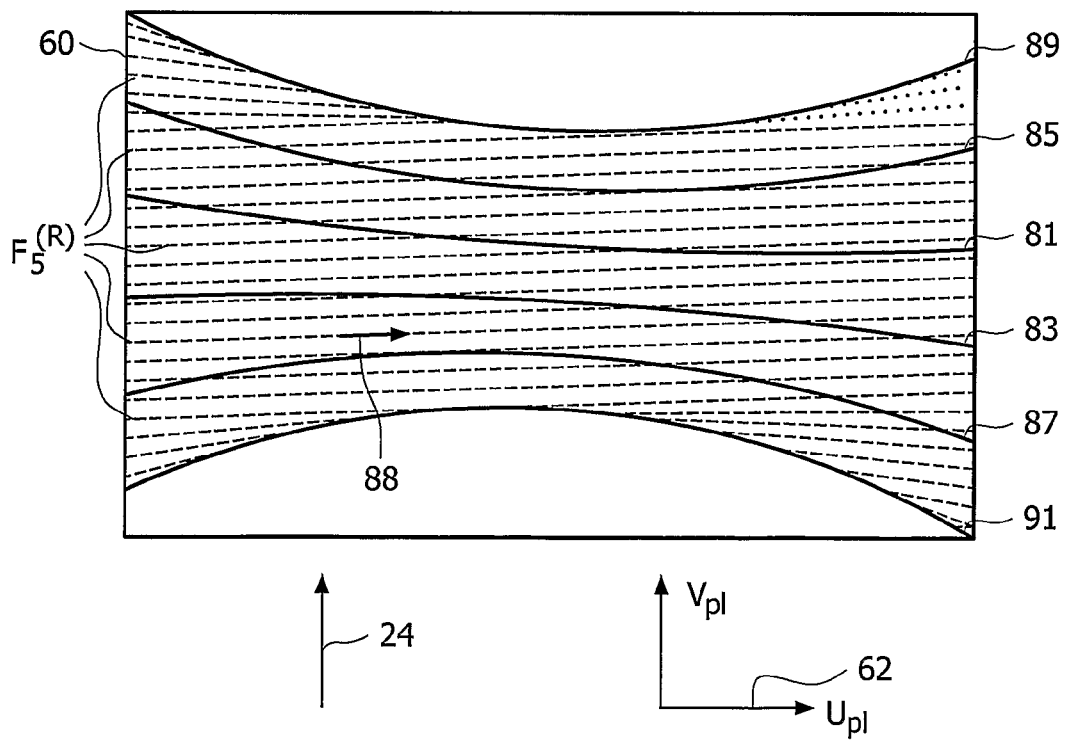
Figure 11:
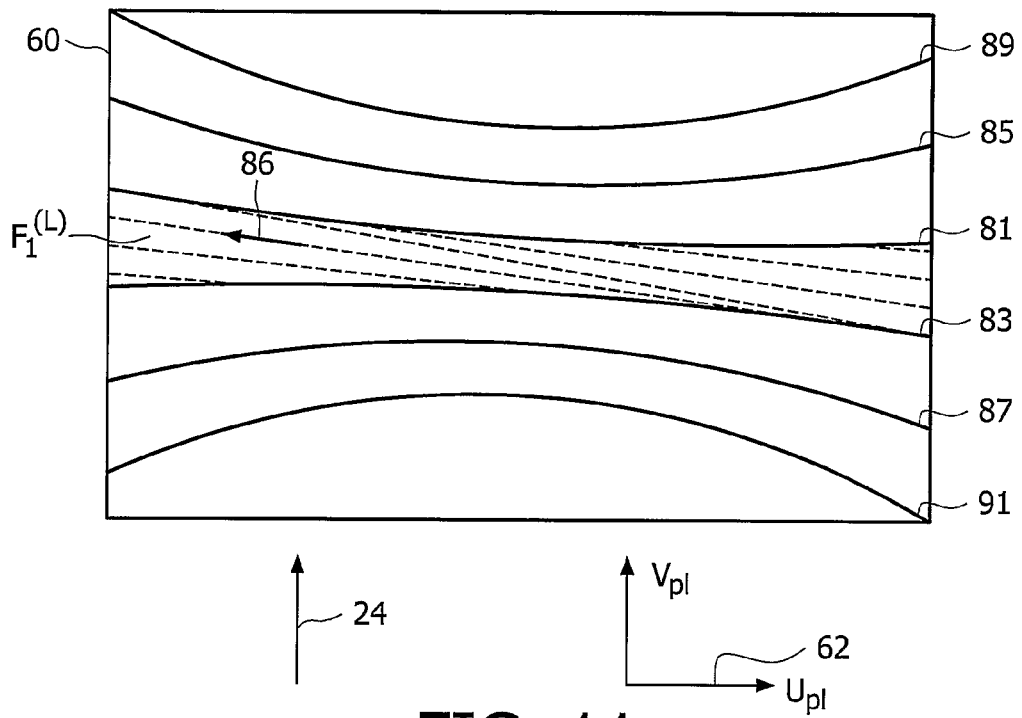
Figure 12:
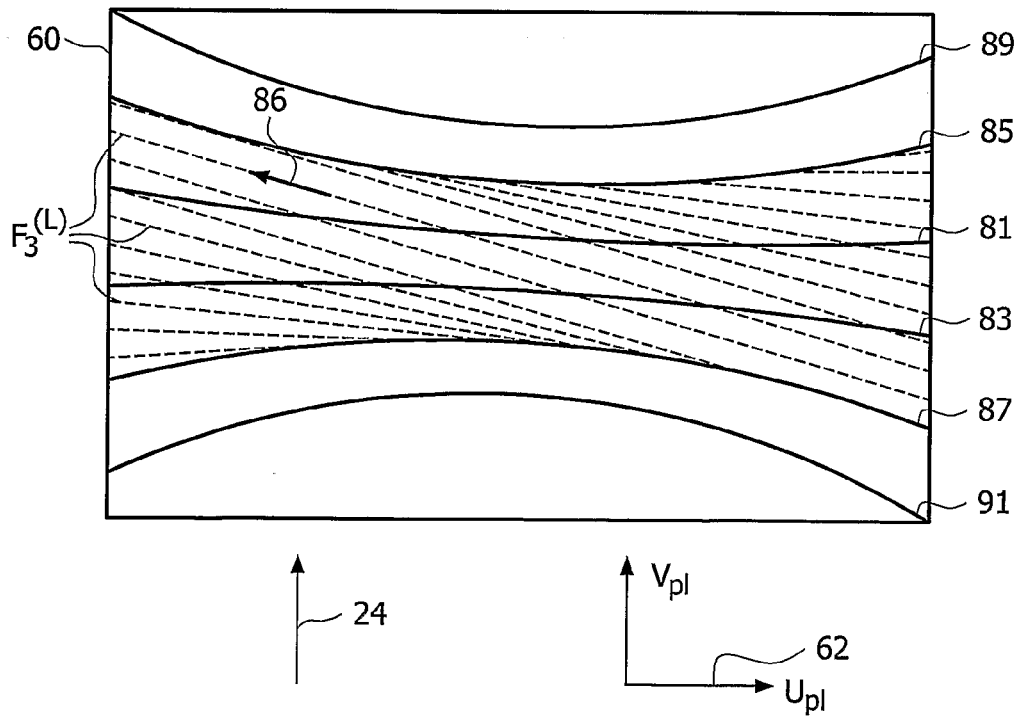

The invention will be elucidated in detail below with the help of drawings. In the drawings, FIG. 1 shows a computer tomograph, by which the method as invented can be executed, FIG. 2 shows a flow chart of the method as invented, FIG. 3 gives a perspective representation of a helical trajectory, a radiation source, a focus-centered and a planar detector surface with a Pi-relative movement, FIG. 4 gives a perspective representation of a helical trajectory, a radiation source, a focus-centered and a planar detector surface with a 3Pi-relative movement, FIG. 5 gives a perspective representation of parallel rays, which emanate from different radiation source positions and meet at the same detector line, FIG. 6 gives a perspective view of a section of the helical trajectory, the radiation source and the planar detector surface, FIG. 7 shows the path of mPi-boundary lines and of pitch lines on the planar detector surface for a 5Pi relative movement, FIGS. 8 to 12 show a path of filter lines for a 5Pi relative movement.

Figure 13:
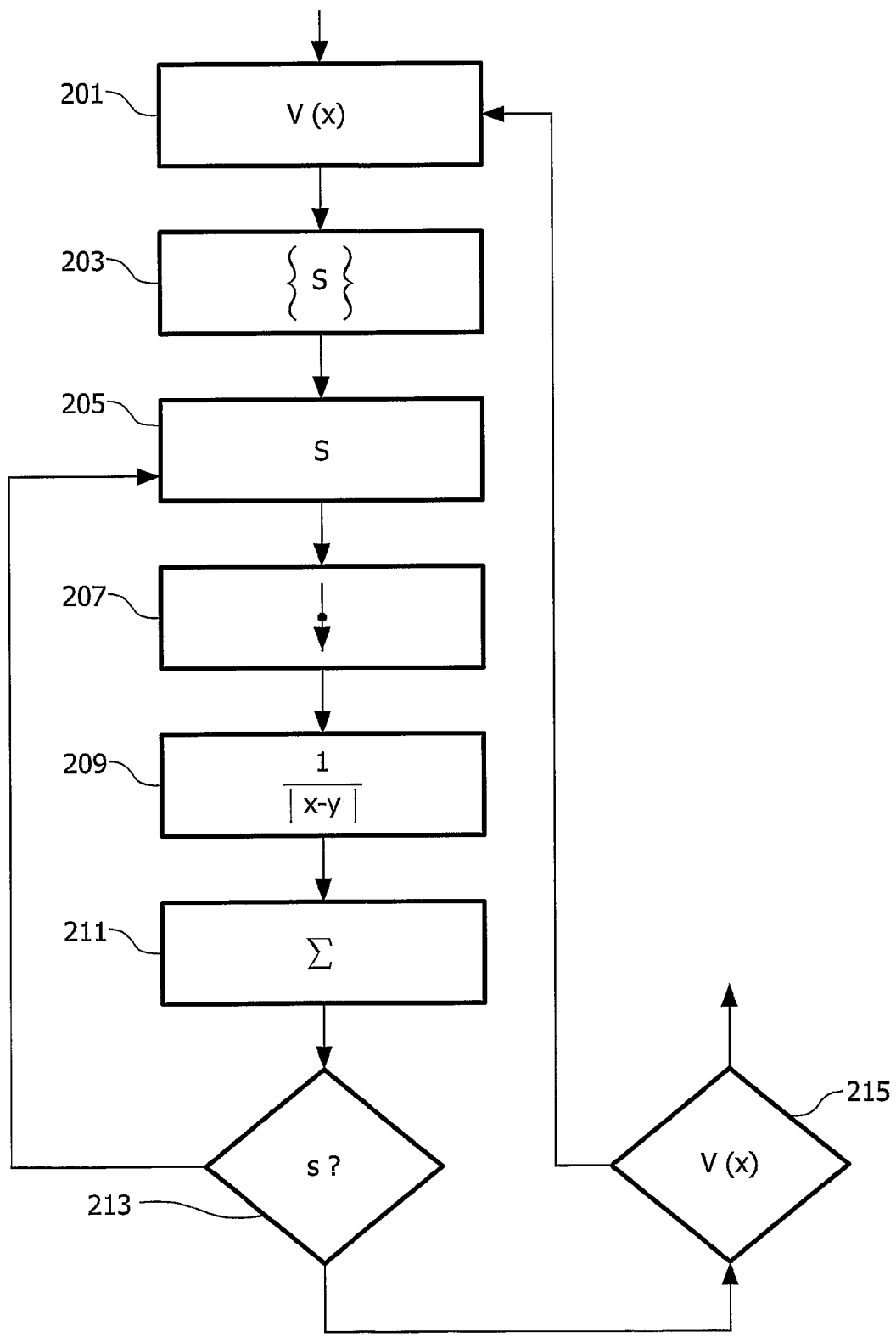

FIG. 13 shows a flow chart of a filtered back projection.

The computer tomograph shown in FIG. 1 comprises a gantry, which can rotate around an axis of rotation 14 running parallel to the z direction of the coordinate system 22 shown in FIG. 1. For this purpose, the gantry 1 is driven by a motor 2 with a preferably constant but adjustable angular velocity. A radiation source S is fastened to the gantry 1, e.g. an X-ray emitter. This is provided with a collimator arrangement 3, which fades out a conical beam 4 from the radiation generated by the radiation source S, i.e. a beam which has a non-zero endless extension in the z direction as well as in a direction perpendicular to it (i.e. in a plane perpendicular to the axis of rotation).

The beam 4 penetrates a cylindrical examination area 13 in which an object, for example a patient, can be present on a patient examination table (neither is shown) or even a technical object. After the penetration of the examination area 13, the beam 4 meets a detector unit 16 fastened to the gantry 1, which detector area comprises a multiplicity of detector elements, which are arranged in the form of a matrix in rows and columns in this embodiment. The detector columns run parallel to the axis of rotation 14. The detector rows are in planes perpendicular to the axis of rotation, in this embodiment on an arc around the radiation source S (focus-centered detector surface). In other embodiments, it could, however, be formed differently e.g. a circular arc around the described axis of rotation 14 or rectilinear. Each detector element hit by the beam delivers a measured value for a ray from the beam 4 in every radiation source position.

The opening angle referred to as $\alpha_{max}$ of the beam 4, defines the diameter of the object cylinder, within which the object to be examined is located when the measured values are acquired. The opening angle is then defined as the angle enclosed by a ray lying at the edge of the beam 4 in a plane at right angles to the axis of rotation 14 with a plane defined by the radiation source S and the axis of rotation 14. The examination area 13 or the object or the patient table can be shifted by means of a motor 5 parallel to the axis of rotation 14 or to the Z axis. But equivalent to this also the gantry can be shifted in this direction. If this is a technical object and not a patient, the object can be rotated for an examination, while the radiation source S and the detector unit 16 are at rest.

If the motors 2 and 5 run simultaneously, the radiation source S and the detector unit 16 describe a helical trajectory 17 in relation to the examination area 13. If, on the other hand, the motor 5 for the feed in the direction of the axis of rotation 14 is at rest and the motor 2 lets the gantry rotate, there is a circular trajectory for the radiation source S and the detector unit 16 in relation to the examination area 13. Only the helical trajectory is taken into consideration below.

The helical trajectory 17 can be parameterized by using $$y(s) = \begin{pmatrix} R\cos s \\ R\sin s \\ s\frac{h}{2\pi} \end{pmatrix} \quad (1)$$

where R is the radius of the helical trajectory 17, s is the angular position on the helical trajectory and h is the pitch, i.e. the distance between two neighboring windings of the helical trajectory.

The measured values acquired by the detector unit 16 are fed to an image processing computer 10, which is linked to the detector unit 16, for example, through data transfer working by the non-contact method (not shown). The image-processing computer 10 reconstructs the absorption distribution in the examination area 13 and displays it, for example on a monitor 11. The two motors 2 and 5, the image processing computer 10, the radiation source S and the transfer of the measured values from the detector unit 16 to the image processing computer 10 are controlled by a control unit 7.

In other embodiments, the acquired measured values for reconstruction can first be fed to one or more reconstruction computers, which forward the reconstructed data e.g. through an optical fiber cable to the image processing computer.

The individual steps of an embodiment of the computerized tomography method as invented are elucidated below with the help of a flow chart in FIG. 2.

After the initialization in step 101 the gantry rotates with an angular velocity, which is constant in this example of embodiment. It can, however, also vary e.g. in relation to time or the position of the radiation source.

In step 103 the examination area or the patient table is shifted parallel to the axis of rotation 14 in the direction of shifting 24 (as opposed to the direction of the Z axis of the coordinates system 22 in FIG. 1) and the radiation of the radiation source S is switched on, such that the detector unit 16 can detect the radiation from a multiplicity of angular positions s and the radiation source S moves on the helical trajectory 17 in relation to the examination area 13.

The pitch h is selected such that at least four neighboring windings of the helical trajectory 17 are projected on the detector surface for each radiation source position y(s). If four windings are projected on the detector surface, then this is a 3Pi-acquisition or -relative movement (FIG. 4). If n+1 windings are projected on the detector surface, where n is an odd integer greater than or equal to 3, then the acquisition is designated as an nPi-acquisition and the relative movement as an nPi-relative movement.

In the framework of the invention, the term nPi acquisition or nPi relative movement comprises relative movements with a pitch selected such that measured values also lying outside the nPi window can be acquired. This term also comprises relative movements with a pitch selected such that measured values are exclusively acquired that lie within the nPi window.

In an nPi-relative movement or acquisition, n is an odd, natural number greater than or equal to 3.

If the pitch h were to be selected such that only two windings were to be projected on the detector surface 16, then the acquisition would be designated as Pi acquisition and the relative movement as Pi-relative movement (FIG. 3). In case of a Pi acquisition, the known κ-method for reconstruction of the measured values mentioned in the opening paragraph can be used.

The path of the projections of the individual windings on a fictitious, planar detector surface 60, whose surface normal intersects the respective radiation source positions y(s) and which contains the axis of rotation 14, can be described by the following equations:

$$v_{P1}(u_{P1}) = +\frac{h}{2\pi}\left(1 + \left(\frac{u_{P1}}{R}\right)^2\right)\left(m\frac{\pi}{2} - \arctan\frac{u_{P1}}{R}\right) \quad (2)$$

and $$v_{P1}(u_{P1}) = -\frac{h}{2\pi}\left(1 + \left(\frac{u_{P1}}{R}\right)^2\right)\left(m\frac{\pi}{2} + \arctan\frac{u_{P1}}{R}\right). \quad (3)$$

Here, $u_{Pl}$ and $v_{Pl}$ are coordinates of a Cartesian coordinate system 62 on the planar detector surface 60, where the $u_{Pl}$-coordinate axis is oriented perpendicularly and the $v_{Pl}$-coordinate axis parallel to the axis of rotation 14. This coordinate system 62 is shown in the FIGS. 7-12 below the planar detector surface 60 for the sake of clarity. The origin of the coordinates system 62 lies, however, in the center of the detector surface 60. The size of the planar detector surface 60 is selected such that all rays that hit the focus-centered detector surface 16 also intersect the planar detector surface 60.

The relation of the coordinates on the fictitious planar detector surface 60 to the coordinates of the real focus-centered detector surface 16 is given by the following equations:

$$u_{P1} = R\tan\beta \quad (4)$$

and $$v_{P1} = \sqrt{R^2 + u_{P1}^2}\tan\lambda = R\frac{\tan\lambda}{\cos\beta} = \frac{v_F}{\cos\beta}\frac{R}{D}. \quad (5)$$

Here, λ is the cone angle of a ray existing from y(s), i.e. the angle that is enclosed by this ray and a plane perpendicular to the axis of rotation 14 and containing the radiation source position y(s). Furthermore, β is the fan angle of a ray exiting from y(s), i.e. the angle enclosed by the projection of this ray on the plane oriented perpendicular to the axis of rotation 14 and containing the radiation source position y(s), and a line that runs through the radiation source position y(s) and is oriented perpendicularly to the axis of rotation 14. The variable D designates the distance of the radiation source position y(s) to the center of the focus-centered real detector surface 16.

With the Pi-acquisition, only two windings neighboring the respective radiation source position y(s) are projected on the real, focus-centered detector surface 16 or on the fictitious planar detector surface 60. The path 81 of the upper projection in FIG. 3 on the planar detector surface 60 is described by equation (2), while the path 83 of the lower projection in FIG. 3 on the planar detector surface 60 is described by the equation (3) (each with m=1). The top projection is further designated as top Pi boundary line 81 and the lower projection is further described as bottom Pi-boundary line 83.

The expressions "top", "below", "left" and "right" and similar expressions relate, in the framework of the invention, to the orientation of the planar detector surface 60 and the associated coordinate system 62, as they are shown in the FIGS. 3, 4, 7 to 12. With this understanding, the direction of shift 24 and the $v_{Pl}$-coordinate axis point to "above". Furthermore, the $u_{Pl}$-coordinate axis points to the "right".

With the Pi-acquisition, four neighboring windings are projected on the real, focus-centered detector surface 16 or on the fictitious planar detector surface 60. The path of the topmost projection 85 in FIG. 4 on the planar detector surface 60 is described by equation (2), while the path of the lowermost projection 87 in FIG. 4 on the planar detector surface 60 is described by the equation (3) (each with n=3). The topmost projection is designated further as top 3Pi boundary line 85 and the lowermost projection is further described as bottom 3Pi-boundary line 87. With the 3Pi-acquisition, a top Pi boundary line 81 and a bottom Pi boundary line 83 and a top 3Pi boundary line 85 and a bottom 3Pi boundary line run on the detector surface.

Accordingly, at the time of an nPi-acquisition, top Pi-, 3Pi-, 5Pi-, . . . , nPi-boundary lines (as in equation (2)) and bottom Pi-, 3Pi-, 5Pi-, . . . , nPi-boundary lines (as in equation (3)) run on the planar detector surface 60.

Top Pi-, 3Pi-, 5Pi-etc. boundary lines have positive $\lambda_{Pl}$-coordinates on the planar detector surface, in contrast to which bottom Pi-, 3Pi-, 5Pi-etc. boundary lines have negative $\lambda_{Pl}$-coordinates.

In case of a 3Pi-acquisition, as shown in FIG. 4, h=57.6 mm can be selected as pitch, if the fan angle of the ray, which bends most strongly from a plane, which contains the axis of rotation 14 and the radiation source position y(s), is 52.1° and if the acquisition geometry is additionally characterized by an extension of the real, focus-centered detector 16 in the direction of the axis of rotation 14 of 175.1 mm, a distance from radiation source position y(s) to the axis of rotation 14 of 570 mm and a distance from radiation source position y(s) to the center of the real, focus-centered detector surface 16 of 1040 mm.

The measured values are derived in step 105 according to the following equation partially according to s, i.e. according to the angular position of the radiation source S:

$$D'_f(y(s), \Theta) = \frac{\partial D_f(y(s), \Theta = const.)}{\partial s} \quad (6)$$

with $$D_f(y(s), \Theta) = \int_0^\infty dl f(y + l\Theta). \quad (7)$$

The $\Theta$ is a unit vector, which differentiates the measured values, which were caused by rays emitted from the same radiation source position, but hit different detector elements. The unit vector $\Theta$ thus indicates the direction of the ray pertaining to the measured value. The direction of the unit vector, i.e. the direction of a ray, can be parameterized ($\Theta=\Theta(s,x)$) by the angular position s of the radiation source on the helical trajectory 17 and by means of a position x in the examination area 13, through which the ray passes. Furthermore, $D_f(y(s), \Theta)$ describes the measured value for a certain radiation source position y(s) and a certain ray direction $\Theta$, which has been measured by means of the focus-centered detector, after the corresponding ray has passed through the object to be reconstructed with the absorption distributions f(x).

In the case of partial derivation of the measured values as given in equation (6), it should be observed that $\Theta$ remains constant, so respective measured values of parallel rays must be taken into consideration for the derivation. Since parallel rays always have the same cone angle, parallel rays 51 meet the same detector line 53 in case of the focus-centered detector surface 16 used here (refer to FIG. 5, in which only one partial area of the detector surface 16 is shown). For partial derivation, the measured values can therefore be re-sorted first. For this purpose, measured values pertaining to parallel rays 51, thus to the same detector line 53 but to different angular positions $s_a$, $s_b$, $s_c$ of the radiation source, are combined to one quantity each. The measured values of each quantity are then derived e.g. numerically by the known finite element method according to the angle position s of the radiation source, where known smoothening techniques can be used.

In step 107 then the derived measured values are projected along their rays on the fictitious planar detector surface 60.

In step 109 one or more filter lines are assigned to each measured value where each filter line is in turn assigned to a filter direction. The filter lines and filter directions indicate which measured values are taken into consideration in which sequential order according to the following equation, to obtain a filter value P(s,x) for a measured value to be filtered, whose ray, starting from the radiation source position y(s) passes through the position x in the examination area:

$$P(s, x) = \sum_{q=1}^{N_f} \mu_q \int_{-\pi}^{\pi} \frac{d\gamma}{\sin\gamma} D'_f(y(s), \Theta_q(s, x, \gamma)). \quad (8)$$

$N_f$ is here the number of filter lines assigned to the measured value to be filtered, whose ray passes through the position x in the examination area starting from the radiation source position y(s). Moreover, $\mu_q$ is a filter factor, which will be described below in greater detail. Moreover, $\Theta_q(s, x, \gamma)$ is a unit vector which indicates the $q^{th}$ filter line 71 with the associated filter direction for a measured value to be filtered, described above and defined by y(s) and x. Finally, $\gamma$ is the κ-angle, which is enclosed by the direction vector $\Theta(s,x)=\Theta_q(s,x,0)$, which starting from the radiation source position y(s) runs through the position x in the examination area, with the unit vector $\Theta_q(s,x,\gamma)$ (refer to FIG. 6).

The relation between the κ-angle $\gamma$, the $q^{th}$ filter line 71 for a measured value given by y(s) and x and the unit vector $\Theta_q(s,x,\gamma)$ is shown in FIG. 6. If the $q^{th}$ filter line 71 of the measured value given by the radiation source position y(s) and x at the position 73, then $\Theta_q(s,x,0)$ designates the ray that has caused the given measured value and the unit vector $\Theta_q(s,x,\gamma)$ senses the measured values on the $q^{th}$ filter line 71 for different κ-angles $\gamma \neq 0$.

The filter lines and the associated filter directions are defined below for the measured values.

First, a number of straight lines is defined as pitch lines $L_m$, where m can assume odd natural values from 1 to n for an nPi acquisition. $L_1$ runs through the center ($\mu_{Pl}=0$, $\nu_{Pl}=0$) of the planar detector 60 and asymptotically to the top and bottom Pi-boundary line. Furthermore, $L_1$ has a positive slope in relation to the ($\mu_{P1}$, $\nu_{P1}$)-coordinate system 62. This is shown by way of example in FIG. 7, in which a top Pi-boundary line 81, a top 3Pi-boundary line 85, a top 5Pi-boundary line 89, a bottom Pi-boundary line 83, a bottom 3Pi-boundary line 87 and a bottom 5Pi-boundary line 91 of a 5Pi-acquisition can be seen. The line $L_1$ runs similarly parallel to the branch ẏ(s) at the respective current angular position S. For m>1, the lines $L_m$ run parallel to $L_1$ and tangentially to the top in Pi-boundary line. With the 5Pi-acquisition the lines $L_3$ and $L_5$ are defined beside the line $L_1$. Moreover, a number of pitch lines $L_{-m}$ is defined, which run parallel to $L_1$ and tangentially to the bottom mPi-boundary line. The lines $L_{-3}$ and $L_{-5}$ are defined with the 5Pi-acquisition. Furthermore, a pitch line $L_{-1}$ is defined, which is equal to the pitch line $L_1$.

Furthermore, a number of pitch lines $L_{-p}^m$ is defined, which have a negative slope in the orientation of the ($\mu_{P1}$, $\nu_{P1}$)-coordinate system 62 mentioned above and shown in FIGS. 7 to 12 and also run tangentially to the top mPi-boundary line as well as tangentially to the bottom pPi-boundary line, where p and m are natural odd numbers smaller than or equal to n. Pitch lines $L_{-5}^1$, $L_{-3}^1$, $L_{-1}^1$, $L_{-1}^3$ and $L_{-1}^5$ are shown in FIG. 7 by way of example.

The slope of a line on the fictitious planar detector surface relates to the $(\mu_{P1}, \nu_{P1})$-coordinate system 62 used here and shown in FIGS. 7 to 12 within the framework of the invention.

In case of an nPi-acquisition, filter lines $F_m^{(L)}$ are defined with m=1, 3, ..., n-2 and $F_m^{(R)}$ where m=1, 3, ..., n, where the filter lines $F_m^{(L)}$ and $F_m^{(R)}$ are arranged exclusively between the top mPi-boundary line and the bottom mPi-boundary line. The filter direction 88 for filter lines $F_m^{(R)}$ runs from left to right on the planar detector surface 60 in the orientation of the detector surface 60 and of the $(\mu_{P1}, \nu_{P1})$-coordinate system 62 shown in the FIGS. 7 to 12, i.e. mostly in the direction of the $\nu_{P1}$-axis of the $(\mu_{P1}, \nu_{P1})$-coordinate system 62. The filter direction 86 for filter lines $F_m^{(L)}$ runs from right to left on the planar detector surface 60 in the orientation of the detector surface 60 and the $(\mu_{P1}, \nu_{P1})$-coordinate system 62 shown in FIGS. 7 to 12, i.e. in essence opposed to the direction of the $\nu_{P1}$-axis of the $(\mu_{P1}, \nu_{P1})$-coordinate system. Some filter directions are indicated by arrows 86, 88 in the FIGS. 8 to 12.

The filter line $F_m^{(L)}$ of a measured value to be filtered according to the equation (8), which lies in the mPi window, runs tangentially to the top 7mPi-boundary line, if the measured value is arranged above the line $L_{-1}^m$. If this is not the case, the filter line runs tangentially to the bottom Pi boundary line, if the measured value is arranged above the $L_{-1}^1$ line. If this is not the case either, the filter line runs tangentially to the top Pi boundary line, if the measured value is arranged above the $L_{-m}^1$ line. If none of the cases described in this paragraph occur, then the filter line $F_m^{(L)}$ runs tangentially to the bottom in mPi-boundary line. Besides, the filter line $F_m^{(L)}$ runs through the measured value to be filtered.

Each filter line $F_m^{(L)}$ thus runs either tangentially to an mPi-boundary line or tangentially to a Pi-boundary line. It is still to be defined, whether the respective filter line $F_m^{(L)}$ approaches the respective Pi or mPi boundary line to the left or right of the measured value to be filtered on the fictitious planar detector, i.e. whether the respective tangential point lies to the left or right of the measured value to be filtered.

For a filter line $F_m^{(L)}$ the respective tangential point lies to the left of the measured value to be filtered, if the filter line $F_m^{(L)}$ runs tangentially to a top mPi- or Pi-boundary line. If the filter line $F_m^{(L)}$, on the other hand, runs tangentially to a bottom mPi- or Pi-boundary line, then the respective tangential point lies to the right of the measured value to be filtered.

The filter line $F_m^{(R)}$ of a measured value to be filtered according to the equation (8), which lies in the mPi window, runs tangentially to the top mPi-boundary line, if the measured value is arranged above the line $F_m^{(R)}$. If this is not the case, the filter line runs parallel to $L_1$, if the measured value is arranged above the $L_{-m}$ line. If this is not the case either, the filter line $F_m^{(R)}$ runs tangentially to the lower mPi boundary line. Besides, the filter line $F_m^{(R)}$ runs through the measured value to be filtered.

Each filter line $F_m^{(R)}$ thus runs either tangentially to an mPi-boundary line or parallel to $L_1$. To determine the position of a tangential point of a filter line $F_m^{(R)}$ running tangentially to a top mPi-boundary line, the tangential point of the pitch line $L_m$ is determined, i.e. the point at which the pitch line $L_m$ touches the top in mPi-boundary line. If the measured value to be filtered is arranged on the fictitious planar detector to the left of this touching point, the tangential point of the filter line $F_m^{(R)}$ lies to the right of the measured value to be filtered. If this is not the case, the tangential point of the filter line $F_m^{(R)}$ lies to the left of the measured value to be filtered on the fictitious planar detector surface.

To determine the position of a tangential point of a filter line $F_m^{(R)}$ running tangentially to a bottom mPi-boundary line, the tangential point of the pitch line $L_{-m}$ is determined, i.e. the point at which the pitch line $L_{-m}$ touches the bottom mPi-boundary line. If the measured value to be filtered is arranged on the fictitious planar detector to the left of this touching point, the tangential point of the filter line $F_m^{(R)}$ lies to the right of the measured value to be filtered. If this is not the case, the tangential point of the filter line $F_m^{(R)}$ lies to the left of the measured value to be filtered on the fictitious planar detector surface.

In case of an nPi-acquisition the filter lines $F_1^{(L)}$, $F_3^{(L)}$, ..., $F_{n-2}^{(L)}$ and $F_1^{(R)}$, $F_3^{(R)}$, ..., $F_n^{(R)}$ are used.

The path of the filter lines is shown by way of example in the FIGS. 8 to 12 for a 5Pi-acquisition, where the filter lines $F_1^{(L)}$ (FIG. 11), $F_3^{(L)}$ (FIG. 12) and $F_1^{(R)}$ (FIG. 8), $F_3^{(R)}$ (FIG. 9), $F_5^{(R)}$ (FIG. 10) are used.

The number of filter lines, which are assigned to a measured value thus depends on its position on the detector surface and the selected "n" for the nPi-acquisition. There are n−m+1 filter lines assigned to a measured value, which lies between two mPi-boundary lines but not between two (m−2) Pi-boundary lines where 1<m≦n, which are filter lines $F_m^{(R)}$, $F_{m+2}^{(R)}$, ..., $F_n^{(R)}$ and $F_m^{(L)}$, $F_{m+2}^{(L)}$, ..., $F_{n-2}^{(L)}$. There are n filter lines assigned to a measured value, which is arranged between the Pi-boundary lines, which filter lines are $F_1^{(R)}$, $F_3^{(R)}$, ..., $F_n^{(R)}$ and $F_1^{(L)}$, $F_3^{(L)}$, ..., $F_{n-2}^{(L)}$ The filter lines $F_1^{(L)}$, $F_3^{(L)}$, $F_1^{(R)}$, $F_3^{(R)}$ and $F_5^{(R)}$ are assigned to a measured value lying between the Pi boundary lines, for the filter lines of a 5Pi acquisition shown in the FIGS. 8 to 12. The filter lines $F_3^{(L)}$, $F_3^{(R)}$ and $F_5^{(R)}$ are assigned to a measured value that does lie between the 3Pi boundary lines, but not between the Pi boundary lines. Finally, the filter line $F_5^{(R)}$ is assigned to a measured value, which lies between the 5Pi-boundary lines but not between the 3Pi boundary lines.

The filter lines $F_m^{(R)}$ and $F_m^{(L)}$ are exclusively dependent on the acquisition geometry used i.e. the dimensions of the computer tomographs and on the selected pitch for a certain location on the detector surface. The filter lines $F_m^{(R)}$ and $F_m^{(L)}$ can thus be determined immediately for known acquisition geometry and not only in step 109.

As the next step, the measured values projected on the planar detector 60 are filtered in step 111 along the predefined filter lines and filter directions according to equation (8).

A measured value to be filtered and a filter line pertaining to this measured value are first selected for this purpose. Along this filter line, measured values lying on the filter line are each multiplied by a κ-factor and summed up in the filter direction. While doing so, the κ-factor decreases with increasing sine of the κ-angle. It is especially equal to the reciprocal of the sine of the κ-angle. The result of the summation is an intermediate filter value. This is repeated for all filter lines of the measured values to be filtered, such that an intermediate filter value is determined for this measured value and for each filter line assigned to this measured value.

The reciprocal of the sine of the κ-angle is designated as κ filter, where also a function that corresponds to the reciprocal of the sine of the κ-angle, but does not represent it exactly, is designated as $\tilde{\kappa}$ filter. For example, the Taylor development of the said reciprocal is also designated as $\tilde{\kappa}$ filter.

Each of these intermediate filter values is multiplied by a filter factor $\mu_q$, where the value of the respective filter factor $\mu_q$ depends on the respective filter line $F_m^{(R)}$, $F_m^{(L)}$. A filter factor $\mu_q = \mu_m^{(R)}$ or $\mu_q = \mu_m^{(L)}$ is assigned to each filter line $F_m^{(R)}$, $F_m^{(L)}$ which factor is defined by the following equations:

$$\mu_m^{(R)} = \begin{cases} \frac{n+1}{4}, m = 1 \\ 1, m = n \\ \frac{1}{2}, \text{else} \end{cases} \quad (9)$$

$$\mu_m^{(L)} = \begin{cases} \frac{n+1}{4}, m = 1 \\ \frac{1}{2}, \text{else} \end{cases} \quad (10)$$

Each intermediate filter value is thus multiplied by the filter factor $\mu_m^{(R)}$ or $\mu_m^{(L)}$ that is assigned to the respective filter line $F_m^{(R)}$ or $F_m^{(L)}$.

The intermediate filter values multiplied by the filter factor are in each case added to a filter value, so that a filter value is assigned to each measured value to be filtered. This method is repeated for each measured value to be filtered till all measured values, lying between the nPi boundary lines at the time of the nPi-acquisition, have been filtered.

For determining a filter value for a measured value to be filtered and a filter line assigned to this measured value, those measured values lying on this filter line are preferably interpolated on the planar detector 60 in such a manner that they are arranged equidistant on this filter line in respect of the κ-angle. Then the interpolated measured values according to equation (8) are multiplied by the κ factor along the filter line and summed to an intermediate filter value, while the multiplication by the κ-factor and the summation can be carried out in a known manner with the help of Fourier transformation.

The filtering was carried out here in the planar detector. It can, however, be executed on any desired detector. In certain cases, the measured values and the filter lines must be projected on this detector. In particular, it could be advisable to filter the measured values on the focus-centered detector, such that the projection of the measured values on the planar detector can be omitted in step 107.

In step 113 the filtered measured values for reconstruction of the absorption distribution in the examination area is backprojected predominantly according to the equation below, where only measured values or filter values are taken into consideration, which lie between the two nPi-lines:

$$f(x) = \frac{(-1)}{2\pi^2} \frac{1}{n} \int \frac{ds}{|x-y(s)|} P(s, x). \quad (11)$$

The back projection is elucidated below with the help of the flow charts shown in FIG. 13.

In step 201 a location x and a Voxel V(x) arranged at this location is predetermined within a predefinable area (field of view—FOV) in the examination area, where a Voxel V(x) is selected, which has not yet been reconstructed in the previous back-projection steps.

Then in step 203 the number of angular positions s or radiation source positions y(s) is defined, from which rays exit, which penetrate the Voxel V(x) centrally and which meet the detector surface between the nPi boundary lines.

Then in step 205 an angular position s from the quantity defined in step 203 is predetermined for angular positions, which has not yet been used for reconstruction of the Voxel V(x).

In step 207, a filter value is determined for the ray exiting from the radiation source position y(s) defined by the predetermined angular positions and passing through the voxel V(x) in the middle. If the detector surface is composed of several rectangular detector elements assuming a measured value each, as in this example of embodiment, the filter value of the measured value picked up from this detector pixel is determined for this ray, if the ray hits a detector element in the middle. If this ray does not hit a detector element in the middle, then a filter value is determined by interpolation of the filter value, whose measured value has been detected by the detector element which the ray hits, and neighboring filter values, for example by a bilinear interpolation.

The filter value determined in step 207 is multiplied by a weight factor in step 209, which weight factor becomes progressively smaller with increasing distance of the radiation source y(s) from the location x predetermined in step 201. In this embodiment, this weight factor, according to equation (11), is equal to $1/|x-y(s)|$.

In step 211 the weighted filter value is added to the voxel V(x), which can initially be equal to zero.

In step 213 it is checked whether all angular positions s from the number of angular positions determined in step 203 have been taken into consideration for the reconstruction of the voxel V(x). If this is not the case, then the flow chart branches at step 205. Otherwise a check is made in step 215 whether all voxels V(x) have been reconstructed in FOV. If not, step 201 is proceeded with. If, on the other hand, all voxels V(x) have been run in the FOV, then the absorption has been determined in the entire FOV and the back projection and thus the computerized tomography method as invented is terminated (step 113).

The invention claimed is:

1. A Computerized tomography method comprising the steps of:
    generating a conical beam traversing an examination area by means of a radiation source;
    generating a helical nPi relative movement between the radiation source and the examination area;
    acquiring measured values, which depend on the intensity in the beam by means of a detector unit, where a ray of the beam is assigned to each measured value; and
    reconstructing a CT image by means of the steps of:
    performing a partial derivation of the measured values according to the angular position of the radiation source;
    generating intermediate filter values, where an intermediate filter value is generated by filtering a derived measured value, which lie in an nPi window, along an associated filter line with a κ-filter, and where, for at least one of those derived measured values, more than one filter line is associated;
    multiplying each intermediate filter value by a corresponding different filter factor, where each intermediate filter value that has been generated is multiplied by its corresponding filter factor, which is greater than or equal to the filter factors by which the other intermediate filter values are multiplied;
    adding the weighted intermediate filter values of each measured value that lies in the nPi window to each respective filter value; and
    reconstructing the CT image by back-projection of the filter values.

2. The computerized tomography method as claimed in claim 1, wherein the generation of an intermediate filter value for a measured value and a filter line by means of a κ-filter has the following steps of:

multiplying those measured values that are arranged along the filter line by a weight factor, wherein the weight factor is equal to the reciprocal value of the sine of the respective κ-angle; and adding the measured values multiplied by the weight factor to an intermediate filter value.

3. The computerized tomography method as claimed in claim 1, wherein the assignment of one or more filter lines to a measured value has the following steps of:

determining pitch lines $L_m$, $L_{-m}$ and $L_{-p}^m$ where m=1, 3, ..., n and p=1, 3, ..., n, where the projections of these lines on a fictitious planar detector surface, which contains the axis of rotation and whose surface normal runs through the respective radiation source position y(s), run as follows:

the projection of the pitch line $L_1$ is parallel to the projection of the branch ẏ(s) of the radiation source position on the planar detector surface;

the projection of the pitch line $L_{-1}$ is equal to the projection of the pitch line $L_1$;

the projection of the pitch line $L_m$ for m>1 is parallel to the projection of $L_1$ and tangential to the projection of the top mPi-boundary line on the planar detector surface;

the projection of the pitch line $L_{-m}$ for m>1 is parallel to the projection of $L_1$ and tangential to the projection of the bottom mPi-boundary line on the planar detector surface; and the projection of the pitch line $L_{-p}^m$ is tangential to the projection of the top mPi-boundary line on the planar detector surface and tangential to the projection of the bottom pPi-boundary line on the planar detector surface and has a negative slope on the planar detector surface;

assigning filter lines $F_1^{(L)}$ and $F_1^{(R)}$, where l assumes the values 1, 3, ..., n−2, if the measured value lies between the Pi boundary lines and where l assumes the values r, r+2, ..., n−2, if n is greater than 3 and if the measured value lies between two rPi-boundary lines but not between two (r−2) Pi-boundary lines, where r is an odd natural number greater than 1 and smaller than n and where each filter line $F_1^{(L)}$, $F_1^{(R)}$ runs through the measured value; and (i) where the projection of the filter line $F_1^{(L)}$ on the planar detector surface runs tangentially to the projection of the top lPi-boundary line on the planar detector surface, if the measured value lies above the pitch line $L_{-1}^1$;

ii) where the projection of the filter line $F_1^{(L)}$ on the planar detector surface runs tangentially to the projection of the bottom Pi-boundary line on the detector surface, if (i) is not applicable and if the measured value lies above the pitch line $L_{-1}^1$;

iii) where the projection of the filter line $F_1^{(L)}$ on the planar detector surface runs tangentially to the projection of the top Pi-boundary line on the planar detector surface, if i) and ii) are not applicable and if the measured value lies above the pitch line $L_{-1}^1$;

iv) where the projection of the filter line $F_1^{(L)}$ on the planar detector surface runs tangentially to the projection of the bottom lPi-boundary line on the planar detector surface, if i), ii) and iii) are not applicable;

v) where the projection of the filter line $F_1^{(R)}$ on the planar detector surface runs tangentially to the projection of the top lPi-boundary line on the planar detector surface, if the measured value lies above the pitch line $L_1$;

vi) where the projection of the filter line $F_1^{(R)}$ on the planar detector surface runs parallel to the projection of the pitch line $L_1$ on the planar detector surface, if v) is not applicable and if the measured value lies above the pitch line $L_{-1}$; and vii) where the projection of the filter line $F_1^{(R)}$ on the planar detector surface runs tangentially to the projection of the bottom lPi-boundary line on the planar detector surface, if v) and vi) are not applicable;

assigning a filter line $F_n^{(R)}$ to the measured value, if the measured value lies between the two nPi-boundary lines, where the filter line runs through the measured value and either only within or inside and outside the nPi-window.

4. The computerized tomography method as claimed in claim 3, wherein the filter directions of the filter lines $F_1^{(L)}$ projected on the planar detector surface predominantly point from right to left and that the filter directions of the filter lines $F_1^{(R)}$ and of the filter line $F_n^{(R)}$ projected on the planar detector surface predominantly point from left to right.

5. The computerized tomography method as claimed in claim 3, wherein:

a filter factor $\mu_1^{(R)}$ is assigned to each filter line $F_l^{(R)}$ and to each intermediate filter value generated along this filter line by filtering, by which filter factor the intermediate filter value is multiplied, where the filter factor $\mu_1^{(R)}$ is equal to (n+1)/4 for l=1 and else the filter factor $\mu_1^{(R)}$ is equal to ½;

a filter factor $\mu_1^{(L)}$ is assigned to each filter line $F_1^{(L)}$ and to each intermediate filter value generated along this filter line by filtering, by which filter factor the intermediate filter value is multiplied, where the filter factor $\mu_1^{(L)}$ is equal to (n+1)/4 for l=1, and else the filter factor $\mu_1^{(L)}$ is equal to ½; and a filter factor $\mu_n^{(R)}$ equal to 1 is assigned to the filter line $F^{n(R)}$ and to each intermediate filter value generated along this filter line by filtering, by which filter factor the intermediate filter value is multiplied.

6. The computerized tomography method as claimed in claim 3, wherein:

if the projection of the filter line $F_1^{(L)}$ on the planar detector surface runs tangentially to the projection of the top lPi-boundary line or the top Pi-boundary line on the planar detector surface, the projection of the filter line $F^{1(L)}$ in an area approaches the top lPi-boundary line or the top Pi-boundary line, which lies to the left of the projection of the measured value to be filtered on the planar detector surface;

if the projection of the filter line $F_1^{(L)}$ on the planar detector surface runs tangentially to the projection of the bottom lPi-boundary line or the bottom Pi-boundary line on the planar detector surface, the projection of the filter line $F^{1(L)}$ in an area approaches the bottom lPi-boundary line or the bottom Pi-boundary line, which lies to the right of the projection of the measured value to be filtered on the planar detector surface;

if the projection of the filter line $F_1^{(R)}$ on the planar detector surface runs tangentially to the projection of the top lPi-boundary line on the planar detector surface and if the location at which the projection of the pitch line L on the planar detector surface touches the projection of the top lPi-boundary line tangentially; lies to the left of the projection of the measured value to be filtered on the planar detector surface, the projection of the filter line $F^{1(L)}$ in an area of the projection approaches the top lPi-boundary line, which lies to the left of the projection of the measured value to be filtered on the planar detector surface;

if the projection of the filter line $F_1^{(R)}$ on the planar detector surface runs tangentially to the projection of the bottom lPi-boundary line on the planar detector surface and if the location at which the projection of the pitch line $F_1^{(R)}$ on the planar detector surface touches the projection of the bottom lPi-boundary line tangentially, lies to the left of the projection of the measured value to be filtered on the planar detector surface, the projection of the filter line $F_1^{(R)}$ in an area of the projection approaches the bottom lPi-boundary line, which lies to the left of the projection of the measured value to be filtered on the planar detector surfaced;

if the projection of the filter line $F_1^{(R)}$ on the planar detector surface runs tangentially to the projection of the top lPi-boundary line on the planar detector surface and if the location at which the projection of the pitch line $F_1^{(R)}$ on the planar detector surface touches the projection of the top lPi-boundary line tangentially, lies to the right of the projection of the measured value to be filtered on the planar detector surface, the projection of the filter line $F_1^{(R)}$ in an area of the projection approaches the top lPi-boundary line, which lies to the right of the projection of the measured value to be filtered on the planar detector surface; and if the projection of the filter line $F_1^{(R)}$ on the planar detector surface runs tangentially to the projection of the bottom lPi-boundary line on the planar detector surface and if the location at which the projection of the pitch line $F_1^{(R)}$ on the planar detector surface touches the projection of the bottom lPi-boundary line tangentially, lies to the right of the projection of the measured value to be filtered on the planar detector surface, the projection of the filter line $F_1^{(R)}$ in an area of the projection approaches the bottom lPi-boundary line, which lies to the right of the projection of the measured value to be filtered on the planar detector surface.

7. The computerized tomography method as claimed in claim 3, wherein:

the projection of the filter line $F_n^{(R)}$ on the planar detector surface runs tangentially to the projection of the top n Pi-boundary line on the planar detector surface, if the measured value lies above the pitch line $L_n$;

the projection of the filter line $F_n^{(R)}$ on the planar detector surface runs parallel to the projection of the pitch line $L_1$ on the planar detector surfaced, if i) is not applicable and if the measured value lies above the pitch line $L_{-n}$; and the projection of the filter line $F_n^{(R)}$ on the planar detector surface runs tangentially to the projection of the bottom n Pi-boundary line on the planar detector surface, if i) and ii) are not applicable.

8. The computerized tomography method as claimed in claim 7, wherein:

if the projection of the filter line $F_n^{(R)}$ on the planar detector surface runs tangentially to the projection of the top nPi-boundary line on the planar detector surface and if the location at which the projection of the pitch line $L_n$ on the planar detector surface touches the projection of the top nPi-boundary line tangentially, lies to the right of the projection of the measured value to be filtered on the planar detector surface, the projection of the filter line $F_n^{(R)}$ in an area of the projection approaches the top nPi-boundary line, which lies to the right of the projection of the measured value to be filtered on the planar detector surface;

if the projection of the filter line $F_n^{(R)}$ on the planar detector surface runs tangentially to the projection of the bottom nPi-boundary line on the planar detector surface and if the location at which the projection of the pitch line $L_{-n}$ on the planar detector surface touches the projection of the bottom nPi-boundary line tangentially, lies to the right of the projection of the measured value to be filtered on the planar detector surface, the projection of the filter line $F_n^{(R)}$ in an area of the projection approaches the bottom nPi-boundary line, which lies to the right of the projection of the measured value to be filtered on the planar detector surface;

if the projection of the filter line $F_n^{(R)}$ on the planar detector surface runs tangentially to the projection of the top nPi-boundary line on the planar detector surface and if the location at which the projection of the pitch line $L_n$ on the planar detector surface touches the projection of the top nPi-boundary line tangentially, lies to the left of the projection of the measured value to be filtered on the planar detector surface, the projection of the filter line $F_n^{(R)}$ in an area of the projection approaches the top nPi-boundary line, which lies to the left of the projection of the measured value to be filtered on the planar detector surface; and if the projection of the filter line $F_n^{(R)}$ on the planar detector surface runs tangentially to the projection of the top nPi-boundary line on the planar detector surface and if the location at which the projection of the pitch line $L_n$ on the planar detector surface touches the projection of the bottom nPi-boundary line tangentially, lies to the left of the projection of the measured value to be filtered on the planar detector surface, the projection of the filter line $F_n^{(R)}$ in an area of the projection approaches the bottom nPi-boundary line, which lies to the left of the projection of the measured value to be filtered on the planar detector surface.

9. The computer tomography system, particularly for executing the method as claimed in claim 1, comprising:

a radiation source for generating a conical beam traversing an examination area;

a drive arrangement, to have the examination area and the radiation source move relative to each other in a helical way;

a detector unit for acquisition of measured values;

a reconstruction unit for reconstruction of a CT image of the examination area from the measured values acquired from the detector unit; and a control unit for controlling the radiation source, the detector unit, the drive arrangement and the reconstruction unit corresponding to the steps as claimed in claim 1.

10. A computer program for a control unit for controlling a radiation source, a detector unit, a drive arrangement and a reconstruction unit of a computer tomograph for executing the method as claimed in claim 1.

11. A computer readable storage medium containing instructions which, when executed by a computer, cause the computer to perform the steps of:

generating intermediate filter values, where an intermediate filter value is generated by filtering a derived measured value, which lie in an nPi window, along an associated filter line with a κ-filter, and where, for at least one of those derived measured values, more than one filter line is associated;

multiplying each intermediate filter value by a corresponding different filter factor, where each intermediate filter value that has been generated is multiplied by its corresponding filter factor, which is greater than or equal to the filter factors by which the other intermediate filter values are multiplied;

adding the weighted intermediate filter values of each measured value that lies in the nPi window to each respective filter value; and reconstructing a CT image by back-projection of the filter values.

12. The computer readable storage medium of claim 11, wherein the instructions include generating of an intermediate filter value for a measured value and a filter line by means of a κ-filter, having the following steps of:

multiplying the measured values that are arranged along the filter line by a weight factor, wherein the weight factor is equal to the reciprocal value of the sine of the respective κ-angle; and adding the measured values multiplied by the weight factor to an intermediate filter value.

13. The computer readable storage medium of claim 11, wherein the instructions include assigning one or more filter lines to a measured value, having the following steps of:

determining pitch lines $L_m$, $L_{-m}$ and $L_{-p}{}^m$ where m=1, 3, ..., n and p=1, 3, ..., n, where the projections of the lines on a fictitious planar detector surface, which contains the axis of rotation and whose surface normal runs through the respective radiation source position y(s), run as follows:

the projection of the pitch line $L_1$ is parallel to the projection of the branch ẏ(s) of the radiation source position on the planar detector surface;

the projection of the pitch line $L_{-1}$ is equal to the projection of the pitch line $L_1$;

the projection of the pitch line $L_m$ for m>1 is parallel to the projection of $L_1$ and tangential to the projection of the top mPi-boundary line on the planar detector surface;

the projection of the pitch line $L_{-m}$ for m>1 is parallel to the projection of $L_1$ and tangential to the projection of the bottom mPi-boundary line on the planar detector surface; and the projection of the pitch line $L_{-p}{}^m$ is tangential to the projection of the top mPi-boundary line on the planar detector surface and tangential to the projection of the bottom pPi-boundary line on the planar detector surface and has a negative slope on the planar detector surface;

assigning filter lines $F_1^{(L)}$ and $F_1^{(R)}$, where l assumes the values 1, 3, ..., n−2, if the measured value lies between the Pi boundary lines and where l assumes the values r, r+2, ..., n−2, if n is greater than 3 and if the measured value lies between two rPi-boundary lines but not between two (r−2) Pi-boundary lines, where r is an odd natural number greater than 1 and smaller than n and where each filter line $F_1^{(L)}$, $F_1^{(R)}$ runs through the measured value; and (i) where the projection of the filter line $F_1^{(L)}$ on the planar detector surface runs tangentially to the projection of the top lPi-boundary line on the planar detector surface, if the measured value lies above the pitch line $L_{-1}{}^1$;

(ii) where the projection of the filter line $F_1^{(L)}$ on the planar detector surface runs tangentially to the projection of the bottom Pi-boundary line on the detector surface, if i) is not applicable and if the measured value lies above the pitch line $L_{-1}{}^1$;

(iii) where the projection of the filter line $F_1^{(L)}$ on the planar detector surface runs tangentially to the projection of the top Pi-boundary line on the planar detector surface, if i) and ii) are not applicable and if the measured value lies above the pitch line $L_{-1}{}^1$;

(iv) where the projection of the filter line $F_1^{(L)}$ on the planar detector surface runs tangentially to the projection of the bottom lPi-boundary line on the planar detector surface, if i), ii) and iii) are not applicable;

(v) where the projection of the filter line $F_1^{(R)}$ on the planar detector surface runs tangentially to the projection of the top lPi-boundary line on the planar detector surface, if the measured value lies above the pitch line $L_1$;

(vi) where the projection of the filter line $F_1^{(R)}$ on the planar detector surface runs parallel to the projection of the pitch line $L_1$ on the planar detector surface, if v) is not applicable and if the measured value lies above the pitch line $L_{-1}$; and (vii) where the projection of the filter line $F_1^{(R)}$ on the planar detector surface runs tangentially to the projection of the bottom lPi-boundary line on the planar detector surface, if v) and vi) are not applicable;

assigning a filter line $F_n^{(R)}$ to the measured value, if the measured value lies between the two nPi-boundary lines, where the filter line runs through the measured value and either only within or inside and outside the nPi-window.

14. The computer readable medium of claim 13, wherein the filter directions of the filter lines $F_1^{(L)}$ projected on the planar detector surface predominantly point from right to left and that the filter directions of the filter lines $F_1^{(R)}$ and of the filter line $F_n^{(R)}$ projected on the planar detector surface predominantly point from left to right.

15. The computer readable medium of claim 13, wherein:

a filter factor $\mu_1^{(R)}$ is assigned to each filter line $F_1^{(R)}$ and to each intermediate filter value generated along this filter line by filtering, by which filter factor the intermediate filter value is multiplied, where the filter factor $\mu_1^{(R)}$ is equal to (n+1)/4 for l=1 and else the filter factor $\mu_1^{(R)}$ is equal to ½;

a filter factor $\mu_1^{(L)}$ is assigned to each filter line $F_1^{(L)}$ and to each intermediate filter value generated along this filter line by filtering, by which filter factor the intermediate filter value is multiplied, where the filter factor $\mu_1^{(L)}$ is equal to (n+1)/4 for l=1 and else the filter factor $\mu_1^{(L)}$ is equal to ½; and a filter factor $\mu_n^{(R)}$ equal to 1 is assigned to the filter line $F_n^{(R)}$ and to each intermediate filter value generated along this filter line by filtering, by which filter factor the intermediate filter value is multiplied.

16. The computer readable medium of claim 13, wherein:

if the projection of the filter line $F_1^{(L)}$ on the planar detector surface runs tangentially to the projection of the top lpi-boundary line or the top Pi-boundary line on the planar detector surface, the projection of the filter line $F_1^{(L)}$ in an area approaches the top lPi-boundary line or the top Pi-boundary line, which lies to the left of the projection of the measured value to be filtered on the planar detector surface;

if the projection of the filter line $F_1^{(L)}$ on the planar detector surface runs tangentially to the projection of the bottom lPi-boundary line or the bottom Pi-boundary line on the planar detector surface, the projection of the filter line $F_1^{(L)}$ in an area approaches the bottom lPi-boundary line or the bottom Pi-boundary line, which lies to the right of the projection of the measured value to be filtered on the planar detector surface;

if the projection of the filter line $F_1^{(R)}$ on the planar detector surface runs tangentially to the projection of the top lPi-boundary line on the planar detector surface and if the location at which the projection of the pitch line $L_1$ on the planar detector surface touches the projection of the top lPi-boundary line tangentially, lies to the left of the projection of the measured value to be filtered on the planar detector surface, the projection of the filter line $F_1^{(L)}$ in an area of the projection approaches the top lPi-boundary line, which lies to the left of the projection of the measured value to be filtered on the planar detector surface;

if the projection of the filter line $F_1^{(R)}$ on the planar detector surface runs tangentially to the projection of the bottom lPi-boundary line on the planar detector surface and if the location at which the projection of the pitch line $F_1^{(R)}$ on the planar detector surface touches the projection of the bottom lPi-boundary line tangentially, lies to the left of the projection of the measured value to be filtered on the planar detector surface, the projection of the filter line $F_1^{(R)}$ in an area of the projection approaches the bottom lPi-boundary line, which lies to the left of the projection of the measured value to be filtered on the planar detector surface;

if the projection of the filter line $F_1^{(R)}$ on the planar detector surface runs tangentially to the projection of the top lPi-boundary line on the planar detector surface and if the location at which the projection of the pitch line $F_1^{(R)}$ on the planar detector surface touches the projection of the top lPi-boundary line tangentially, lies to the right of the projection of the measured value to be filtered on the planar detector surface, the projection of the filter line $F_1^{(R)}$ in an area of the projection approaches the top lPi-boundary line, which lies to the right of the projection of the measured value to be filtered on the planar detector surface; and if the projection of the filter line $F_1^{(R)}$ on the planar detector surface runs tangentially to the projection of the bottom lPi-boundary line on the planar detector surface and if the location at which the projection of the pitch line $F_1^{(R)}$ on the planar detector surface touches the projection of the bottom lPi-boundary line tangentially, lies to the right of the projection of the measured value to be filtered on the planar detector surface, the projection of the filter line $F_1^{(R)}$ in an area of the projection approaches the bottom lPi-boundary line, which lies to the right of the projection of the measured value to be filtered on the planar detector surface.

17. The computer readable medium of claim 13, wherein:

the projection of the filter line $F_n^{(R)}$ on the planar detector surface runs tangentially to the projection of the top n Pi-boundary line on the planar detector surface, if the measured value lies above the pitch line $L_n$;

the projection of the filter line $F_n^{(R)}$ on the planar detector surface runs parallel to the projection of the pitch line $L_1$ on the planar detector surface, if i) is not applicable and if the measured value lies above the pitch line $L_{-n}$; and the projection of the filter line $F_n^{(R)}$ on the planar detector surface runs tangentially to the projection of the bottom n Pi-boundary line on the planar detector surface, if i) and ii) are not applicable.

18. The computer readable medium of claim 17, wherein:

if the projection of the filter line $F_n^{(R)}$ on the planar detector surface runs tangentially to the projection of the top nPi-boundary line on the planar detector surface and if the location at which the projection of the pitch line $L_n$ on the planar detector surface touches the projection of the top nPi-boundary line tangentially, lies to the right of the projection of the measured value to be filtered on the planar detector surface, the projection of the filter line $F_n^{(R)}$ in an area of the projection approaches the top nPi-boundary line, which lies to the right of the projection of the measured value to be filtered on the planar detector surface;

if the projection of the filter line $F_n^{(R)}$ on the planar detector surface runs tangentially to the projection of the bottom nPi-boundary line on the planar detector surface and if the location at which the projection of the pitch line $L_{-n}$ on the planar detector surface touches the projection of the bottom nPi-boundary line tangentially, lies to the right of the projection of the measured value to be filtered on the planar detector surface, the projection of the filter line $F_n^{(R)}$ in an area of the projection approaches the bottom nPi-boundary line, which lies to the right of the projection of the measured value to be filtered on the planar detector surface;

if the projection of the filter line $F_n^{(R)}$ on the planar detector surface runs tangentially to the projection of the top nPi-boundary line on the planar detector surface and if the location at which the projection of the pitch line $L_n$ on the planar detector surface touches the projection of the top nPi-boundary line tangentially, lies to the left of the projection of the measured value to be filtered on the planar detector surface, the projection of the filter line $F_n^{(R)}$ in an area of the projection approaches the top nPi-boundary line, which lies to the left of the projection of the measured value to be filtered on the planar detector surface; and if the projection of the filter line $F_n^{(R)}$ on the planar detector surface runs tangentially to the projection of the bottom nPi-boundary line on the planar detector surface and if the location at which the projection of the pitch line $L_{-n}$ on the planar detector surface touches the projection of the bottom nPi-boundary line tangentially, lies to the left of the projection of the measured value to be filtered on the planar detector surface, the projection of the filter line $F_n^{(R)}$ in an area of the projection approaches the bottom nPi-boundary line, which lies to the left of the projection of the measured value to be filtered on the planar detector surface.

19. A computed tomography system comprising:

a first component that generates intermediate filter values, where an intermediate filter value is generated by filtering a derived measured value, which lies in an nPi window, along an associated filter line with a κ-filter, and where, for at least one of those derived measured values, more than one filter line is associated;

a second component that multiplies each intermediate filter value by a corresponding different filter factor, where each intermediate filter value that has been generated is multiplied by its corresponding filter factor, which is greater than or equal to the filter factors by which the intermediate filter values are multiplied;

a third component that adds the weighted intermediate filter values of each measured value that lies in the nPi window to each respective filter value; and a fourth component that reconstructs a CT image by backprojection of the filter values.

20. The computed tomography system of claim 19, including:

a radiation source that generates a conical beam traversing an examination area;

a helical nPi relative movement between the radiation source and the examination area; and a detector unit that acquires measure values, which depend on the intensity in the beam and where a ray of the beam is assigned to each measured value.

* * * * *